United States Patent
Lai et al.

(10) Patent No.: US 10,130,524 B1
(45) Date of Patent: Nov. 20, 2018

(54) WIRELESS DETECTABLE DIAPER AND MONITORING EQUIPMENT THEREOF

(71) Applicant: Chung-Ping Lai, Zhubei, Hsinchu Couunty (TW)

(72) Inventors: Chung-Ping Lai, Zhubei (TW); Kuo-Hsin Chang, Dalin Township Chiayi County (TW)

(73) Assignee: Chung-Ping Lai, Hsinchu (TW)

( * ) Notice: Subject to any disclaimer, the term of this patent is extended or adjusted under 35 U.S.C. 154(b) by 0 days.

(21) Appl. No.: 15/640,307

(22) Filed: Jun. 30, 2017

(51) Int. Cl.
*A61F 13/42* (2006.01)
*H04Q 9/00* (2006.01)
*G08B 21/20* (2006.01)

(52) U.S. Cl.
CPC .............. *A61F 13/42* (2013.01); *G08B 21/20* (2013.01); *H04Q 9/00* (2013.01); *A61F 2013/424* (2013.01); *H04Q 2209/47* (2013.01); *H04Q 2209/82* (2013.01)

(58) Field of Classification Search
None
See application file for complete search history.

(56) References Cited

U.S. PATENT DOCUMENTS

| 9,649,230 | B1 * | 5/2017 | Li | A61F 13/42 |
|---|---|---|---|---|
| 2007/0152829 | A1 * | 7/2007 | Lindsay | G06K 19/0717 340/572.3 |
| 2014/0198203 | A1 * | 7/2014 | Vardi | G08B 21/20 348/135 |
| 2017/0214142 | A1 * | 7/2017 | Rokhsaz | H01Q 9/0442 |
| 2018/0021184 | A1 * | 1/2018 | Monson | A61F 13/42 |

* cited by examiner

*Primary Examiner* — Leon-Viet Nguyen

(57) ABSTRACT

A wireless detectable diaper contains: a body and a shiftable-frequency RFID tag. The body includes a water-permeable lining layer, a waterproof layer, and an absorption layer. The RFID tag includes a chip and an antenna, wherein the antenna has a main part and an extending part, the extending part is arranged on a water-absorbing substrate, the extending part and the substrate contact with the absorption layer and are arranged on a wetting position of the body, and the main part and the chip are arranged on a non-wetting position of the body. When the body is not wet, a first frequency reading section of the antenna departs from a second frequency reading section of the monitoring equipment. The substrate absorbs urine or water in the absorption layer and is soaked by the urine or the water, such that a dielectric coefficient of the substrate is changed.

16 Claims, 8 Drawing Sheets

WIRELESS DETECTABLE DIAPER AND MONITORING EQUIPMENT THEREOF

FIELD OF THE INVENTION

The present invention relates to a wireless detectable diaper which reads the radio signal of the RFID tag via the reading antenna, and the reader sends an electrical signal to the notification module, thereafter the notification module sends a notification message (i.e., the body gets wet).

BACKGROUND OF THE INVENTION

A conventional detectable diaper is disclosed in CN103845156 and mates with a radio frequency reader, and the conventional detectable diaper contains two absorption pads corresponding two waist portions of a user, a sensing assembly, and a radio frequency identification (RFID) tag, wherein each of the two absorption pad has a lining layer, a waterproof layer, an absorbing layer defined between the lining layer and the waterproof layer, and a releasable paper defined between the lining layer and the waterproof layer. The sensing assembly includes at least two sensing lines fixed between the lining layer and the waterproof layer, and each of the at least two sensing lines passes through the absorbing layer and its two ends extend to the two waist portions, wherein one of the two ends of each sensing line is located in an accommodation space. The RFID tag is housed in the accommodation space and is electrically connected with each sensing line. When the absorbing layer of the absorption pad absorbs excreta and gets wet, the two sensing lines electrically conduct with each other and form a loop with the RFID tag, wherein the radio frequency reader is configured to read the RFID tag, to detect a change of resistance between the two sensing lines, and to send a notification signal. However, the RFID tag is broken easily.

Another conventional detectable diaper and its detection system are disclosed in TW Patent No. 1533857, the detectable diaper contains a body, at least one chip, at least one metal antenna, and a signal reader. Each of the at least one chip and the metal antenna are attached on an anti-leak layer of the body and are connected together so as to form a RFID tag. When the body is wet, a dielectric coefficient of the anti-leak layer changes so as to change a resistance value of each metal antenna, hence a wavelength of an electromagnetic wave signal from the RFID tag changes, and the signal reader sends the electromagnetic wave to the RFID tag, the RFID tag transmits a response electromagnetic wave back to the signal reader so that the signal reader judges whether the body gets wet. However, the at least one metal antenna cannot receive the electromagnetic wave completely, the detectable diaper cannot exactly judge whether the body fully absorbs urine, and the signal reader constantly receives the response electromagnetic wave to heat the at least one chip quickly.

The present invention has arisen to mitigate and/or obviate the afore-described disadvantages.

SUMMARY OF THE INVENTION

The primary objective of the present invention is to provide a wireless detectable diaper which reads the radio signal of the RFID tag via the reading antenna, and the reader sends an electrical signal to the notification module, thereafter the notification module sends a notification message (i.e., the body gets wet).

To obtain above-mentioned objective, a wireless detectable diaper provided by the present invention contains a body and a shiftable-frequency RFID tag, and the body includes a water-permeable lining layer, a waterproof layer, and an absorption layer defined between the lining layer and the waterproof layer and configured to absorb urine or water.

The RFID tag is a passive ultra-high frequency (UHF) RFID tag and including a chip and an antenna electrically connected with the chip, wherein the antenna has a main part and an extending part, the extending part is arranged on a water-absorbing substrate, the extending part and the substrate contact with the absorption layer of the body, the extending part and the substrate are arranged on a wetting position of the body, and the main part and the chip are arranged on a non-wetting position of the body.

When the body is not wet, a first frequency reading section of the antenna departs from a second frequency reading section of the monitoring equipment.

The substrate absorbs the urine or the water in the absorption layer and is soaked by the urine or the water, hence a dielectric coefficient of the substrate is changed, and frequency deviates to the second frequency reading section of the monitoring equipment from the first frequency reading section of the antenna.

Preferably, the substrate is made of any one of paper, fabric, plastic, fiber, and wood pulp.

Preferably, the second frequency reading section of the monitoring equipment is within 820 MHz to 966 MHz.

Preferably, the antenna is printed on the substrate and is made of conductive ink.

Preferably, the extending part and the substrate are defined between the absorption layer and the waterproof layer or are defined between the absorption layer and the lining layer.

Monitoring equipment of the wireless detectable diaper contains: a reader, a reading antenna electrically connected with the reader, and a notification module electrically connected with the reader, wherein the reader reads a radio signal of the RFID tag via the reading antenna, and the reader sends an electrical signal to the notification module, thereafter the notification module sends a notification message to indicate that the body gets wet.

The monitoring equipment also contains at least one of a speaker and a light emitting element, the speaker and the light emitting element are electrically coupled with the notification module so that the notification module sends the notification message by using the speaker or/and the light emitting element in a sound making manner or a light emitting manner.

The monitoring equipment contains a wireless communication module electrically connected with the notification module, wherein after the reader reads the radio signal of the RFID tag, it sends an electric signal to the notification module, and the notification module transmits the notification message via the wireless communication module.

The monitoring equipment further contains a camera communicatively connected with the notification module, and the camera takes an image after the notification module transmits the notification message which is the body gets wet.

The monitoring equipment further contains a camera communicatively connected with the notification module, and the camera takes an image after the notification module transmits the notification message which is the body gets wet.

Preferably, the camera is communicatively connected with the notification module in a wired signal transmission manner or a wireless signal transmission manner.

DETAILED DESCRIPTION OF THE PREFERRED EMBODIMENTS

Figure 1:
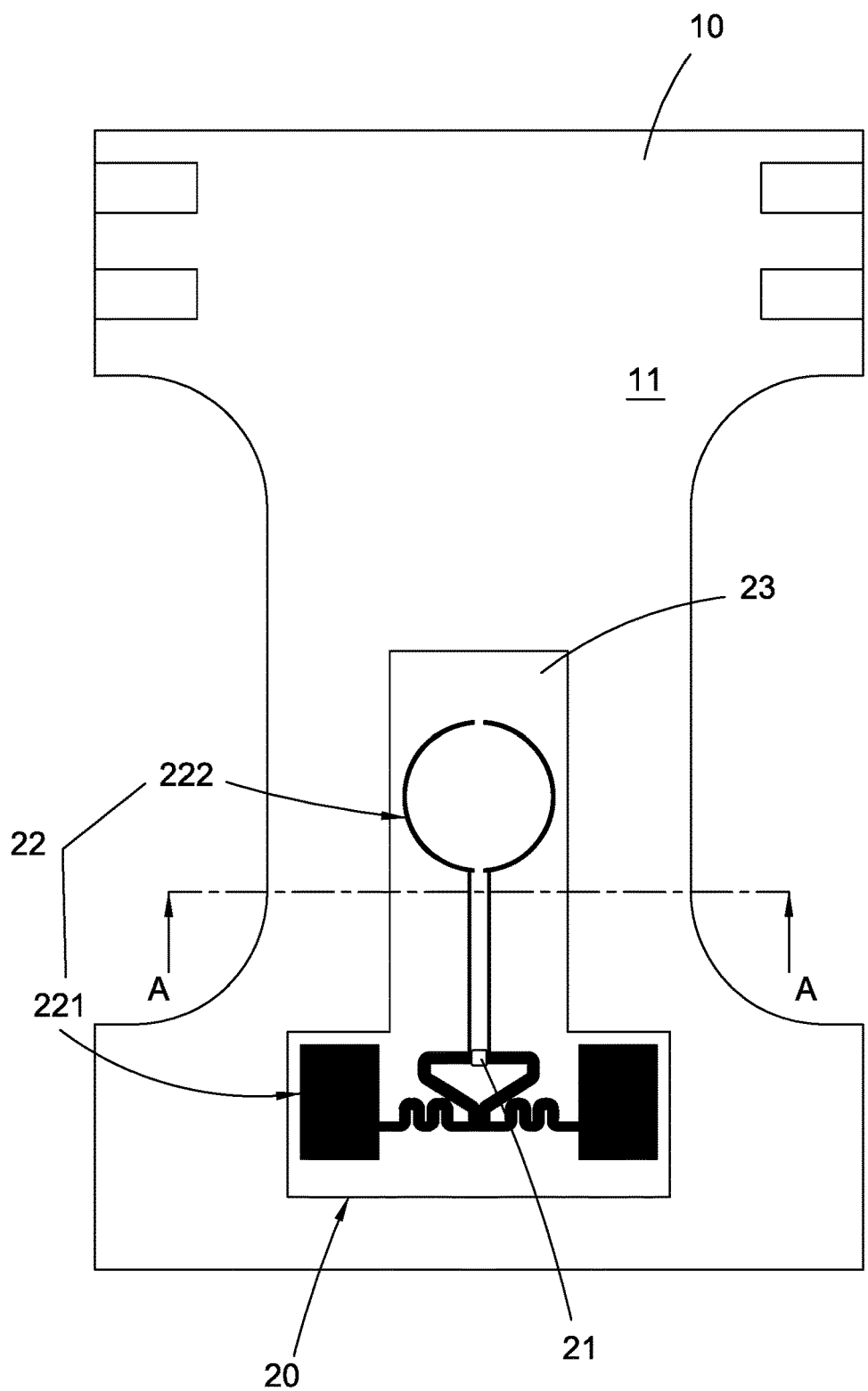
FIG. 1 is a schematic view showing the assembly of a wireless detectable diaper according to a preferred embodiment of the present invention.
Figure 2:
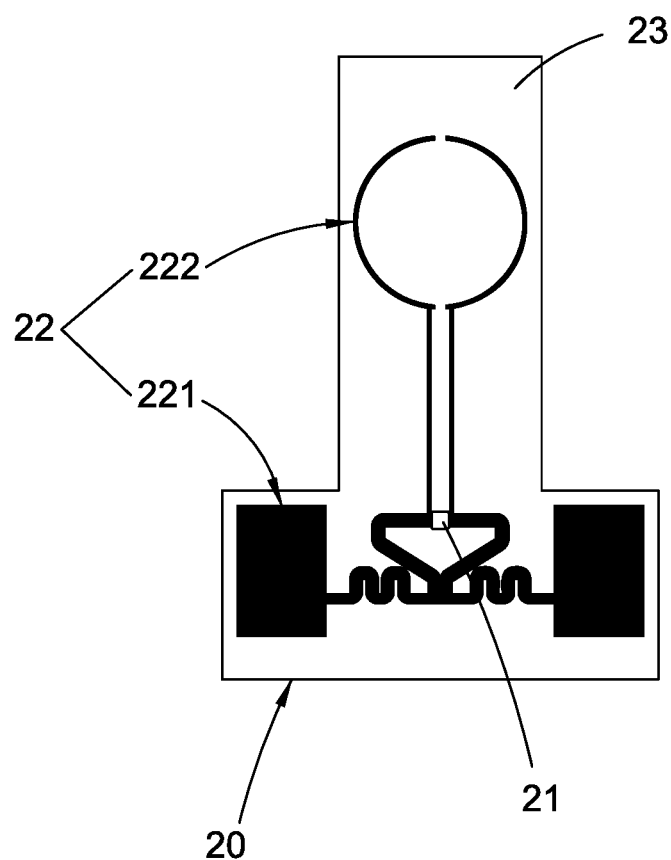
FIG. 2 is a schematic view showing the assembly of a part of the wireless detectable diaper according to the preferred embodiment of the present invention.

With reference to FIGS. 1 and 2, a wireless detectable diaper according to a preferred embodiment of the present invention comprises: a body 10 and a shiftable-frequency RFID tag 20.

The body 10 includes a water-permeable lining layer 11, a waterproof layer 12, and an absorption layer 13 defined between the lining layer 11 and the waterproof layer 12 and configured to absorb urine or water.

Figure 6:
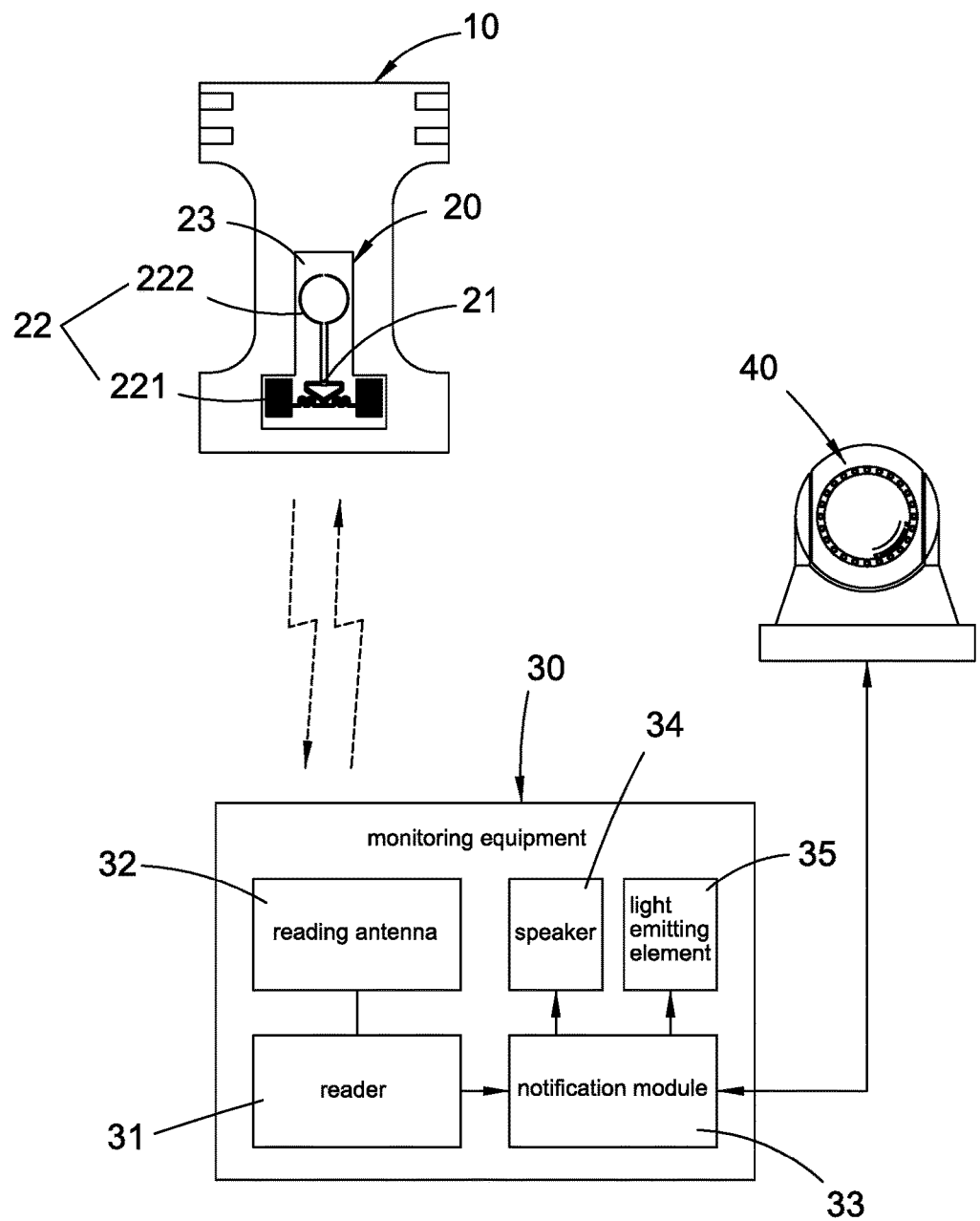
FIG. 6 is a block diagram showing the assembly of the wireless detectable diaper and monitoring equipment of the wireless detectable diaper according to a preferred embodiment of the present invention.

The RFID tag 20 includes a chip 21 and an antenna 22 electrically connected with the chip 21, wherein the antenna 22 has a main part 221 and an extending part 222, when the body 10 is not wet, a first frequency reading section of the antenna 22 departs from a second frequency reading section of monitoring equipment (as shown in FIG. 6); wherein the second frequency reading section of the monitoring equipment is a ultra-high frequency (UHF) within 860 MHz to 960 MHz, however, the UHF is different based on regulation of various regions and countries, for example, the UHF is within 820 MHz to 966 MHz in Taiwan. Preferably, the RFID tag 20 is a passive UHF RFID tag.

The main part 221 and the extending part 222 of the antenna 22 are arranged on a water-absorbing substrate 23 which is made of any one of paper, fabric, plastic, fiber, and wood pulp, wherein the extending part 222 is printed on the substrate 23 and is made of conductive ink having any one of conductive carbon, Nano silver, and Nano copper. The extending part 222 and the substrate 23 contact with the absorption layer 13 of the body 10 so that the substrate 23 absorbs the urine or the water in the absorption layer 13 and is soaked by the urine or the water, thus changing dielectric coefficient of the substrate 23 and deviating frequency to the second frequency reading section of the monitoring equipment from the first frequency reading section of the antenna 22.

Figure 3:
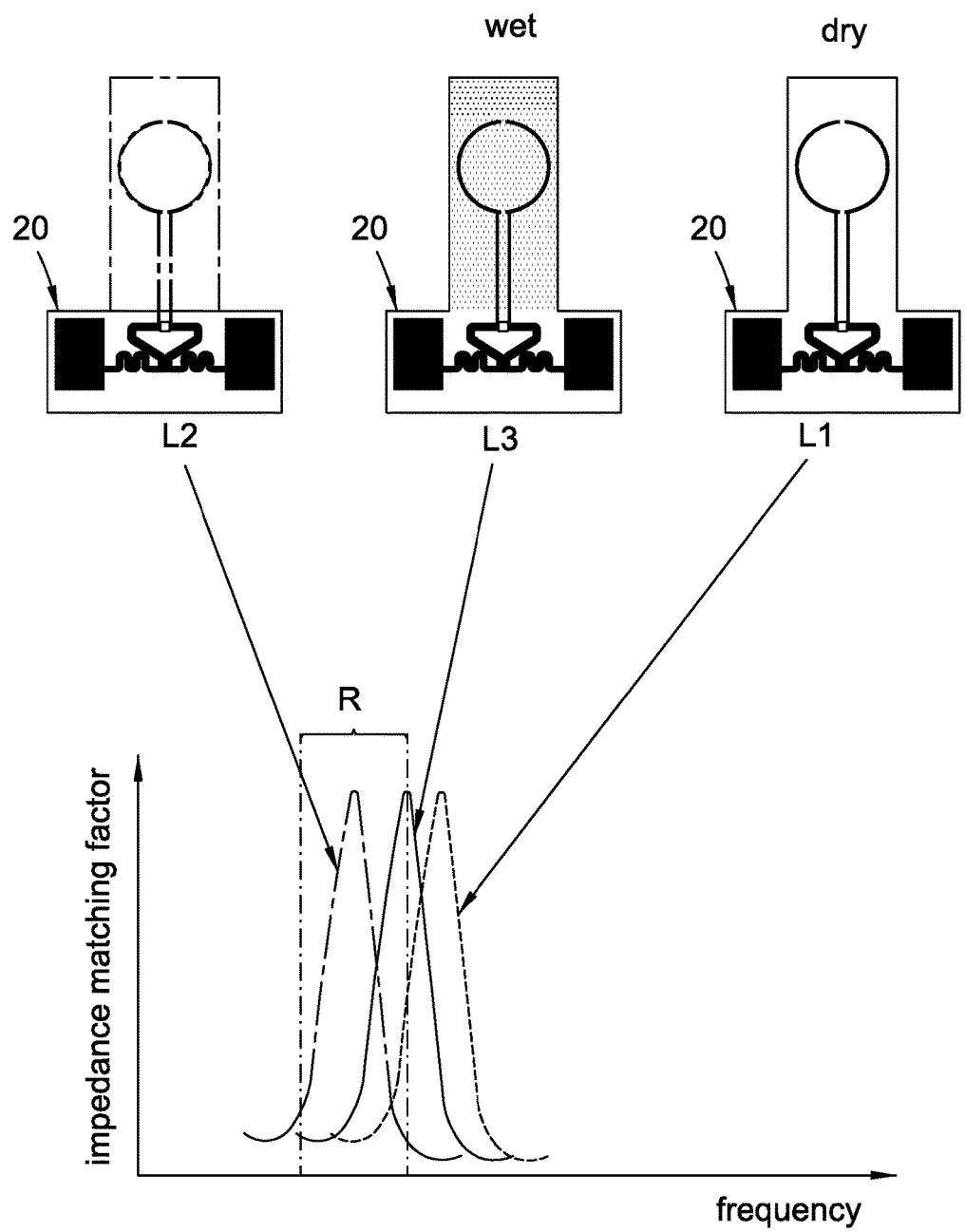
FIG. 3 is a schematic view showing the operation of a part of the wireless detectable diaper according to the preferred embodiment of the present invention.

Referring to FIG. 2, when the body 10 is not wet, the first frequency reading section (indicated by a first dotted line L1 of FIG. 3) of the RFID tag 20 departs from the second frequency reading section R of the monitoring equipment. The main part 221 connects with the extending part 222, and the main part 221 and the extending part 222 are electrically coupled with the chip 21. When the body 10 is not wet, the main part 221 and impedance matching of the extending part 222 of RFID tag 20 is within the second frequency reading section R of the monitoring equipment, and a read distance is 50 cm.

When the antenna 22 of the RFID tag 20 only has the main part 221, the first frequency reading section (designed by a second dotted line L2 of FIG. 3) of the main part 221 and the chip 21 of RFID tag 20 is within the second frequency reading section R of the monitoring equipment.

The dielectric coefficient of the substrate 23 is changed, after the substrate 23 absorbs the urine or the water and the water absorbs radio wave. The antenna 22 of the RFID tag 20 offsets its frequency after the extending part 222 of the substrate 23 is wet, hence the first frequency reading section of RFID tag 20 offsets to the second frequency reading section R (shown by a solid line L3 of FIG. 3) of the monitoring equipment, and a distance of the first frequency reading section of the RFID tag 20 increases. For example, the distance of the first frequency reading section of the RFID tag 20 is 3 m, and the monitoring equipment sends notification message (i.e., the body gets wet) after reading a radio signal of the RFID tag 20.

In another embodiment, the main part 221 and the extending part 222 are made of metal material (such as copper and aluminum) in an etching manner or a plating manner, and the substrate 23 is made of the plastic. For example, the main part 221 and the extending part 222 are fixed on a releasable carrier of plastic and are adhered onto the substrate 23 from the releasable carrier.

The extending part 222 and the substrate 23 are arranged on a wetting position (i.e., an absorbing position of the body 10), and the main part 221 and the chip 21 are arranged on a non-wetting position (i.e., on a peripheral side of the body 10 correspond to user's belly or back).

Figure 4:
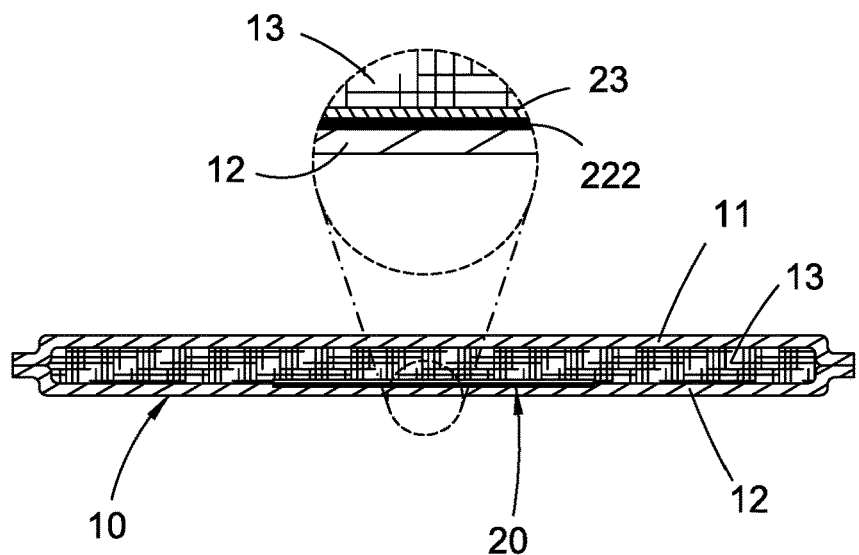
FIG. 4 is a cross sectional taken along the line of A-A of FIG. 1.
Figure 5:
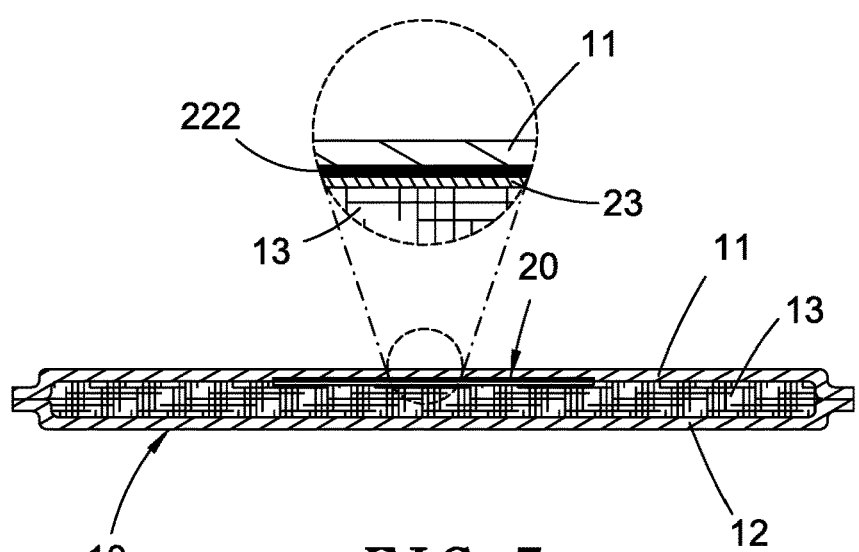
FIG. 5 is a schematic view showing the structure of FIG. 4.

With reference to FIG. 4, the extending part 222 and the substrate 23 are defined between the absorption layer 13 and the waterproof layer 12, for instance, the extending part 222 is located below the absorption layer 13. As illustrated in FIG. 5, the extending part 222 and the substrate 23 are defined between the absorption layer 13 and the lining layer 11, for example, the extending part 222 is located above the absorption layer 13.

Referring to FIG. 6, the monitoring equipment 30 comprises a reader 31, a reading antenna 32 electrically connected with the reader 31, and a notification module 33 electrically connected with the reader 31, wherein the reader 31 is a radio frequency identification (RFID) reader which reads the radio signal of the RFID tag 20 via the reading antenna 32, and the reader 31 sends an electrical signal to the notification module 33, thereafter the notification module 33 sends a notification message (i.e., the body 10 gets wet).

The reader 31 transmits a radio frequency signal in a predetermined time and reads the radio signal of the RFID tag 20. When the body 10 is dry, the first frequency reading section of RFID tag 20 departs from a third frequency reading section of the reader 31, so the reader 31 does not read the radio signal of the RFID tag 20. After the body 10 gets wet, the first frequency reading section of the RFID tag 20 offsets to the third frequency reading section of the reader 31 so that the reader 31 reads the radio signal of the RFID tag 20 and sends the electric signal to the notification module 33, then the notification module 33 transmits the notification message (i.e., the body gets wet).

The monitoring equipment 30 also comprises at least one of a speaker 34 and a light emitting element 35, and the light emitting element 35 is a light bulb or light emitting diode. The speaker 34 and the light emitting element 35 are electrically coupled with the notification module 33 so that the notification module 33 sends the notification message (i.e. the body get wets) to a user by using the speaker 34 or/and the light emitting element 35 in a sound making manner or a light emitting manner.

Figure 7:
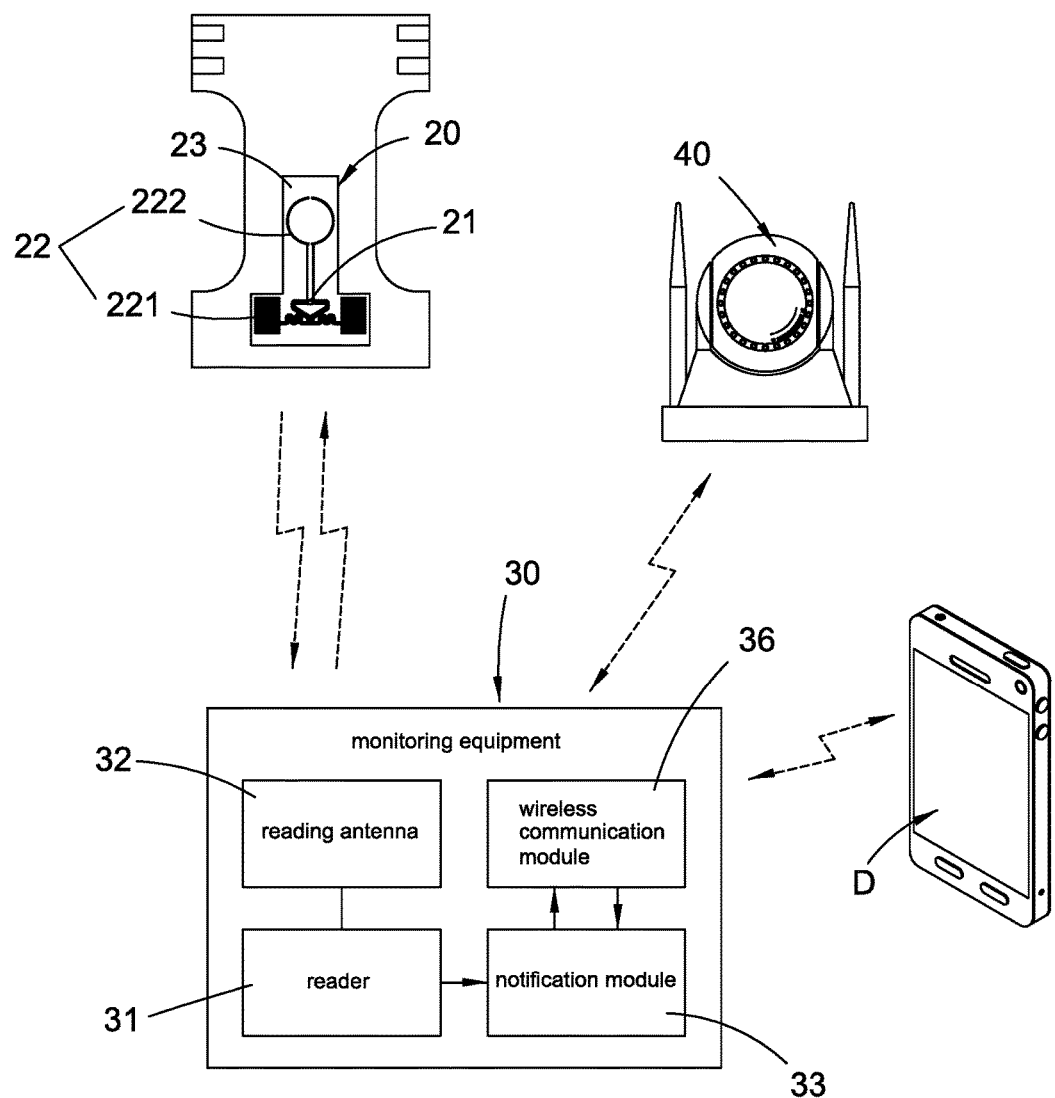
FIG. 7 is a block diagram showing the assembly of the wireless detectable diaper and monitoring equipment of the wireless detectable diaper according to another preferred embodiment of the present invention.

Referring to FIG. 7, the monitoring equipment 30 comprises a wireless communication module 36 electrically connected with the notification module 33. The wireless communication module 36 is a bluetooth communication module or a Wi-Fi communication module. After the reader 31 reads the radio signal of the RFID tag 20, it sends an electric signal to the notification module 33, and the notification module 33 transmits the notification message (e.g., the body gets wet) via the wireless communication module 36. Preferably, the wireless communication module 36 is communicatively in connection with an electronic device D so as to send the notification message to the electronic device D or (application) APP of the electronic device D. The electronic device D is any one of a smart phone, a personal computer, a tablet computer, and a laptop computer.

The monitoring equipment 30 further comprises a camera 40 communicatively connected with the notification module 33, wherein the camera 40 takes an image after the notification module 33 transmits the notification message (e.g., the body gets wet). Preferably, the camera 40 is an internet camera which sends the image to an image display device of the monitoring equipment 30 via an internet, and the image display device is any one of a smart phone, a personal computer, a tablet computer, and a laptop computer.

As shown in FIG. 6, the camera 40 is communicatively connected with the notification module 33 in a wired signal transmission manner. As illustrated in FIG. 7, the camera 40 is communicatively connected with the notification module 33 via the wireless communication module 36 of the monitoring equipment 30 in a wireless sending manner.

Figure 8:
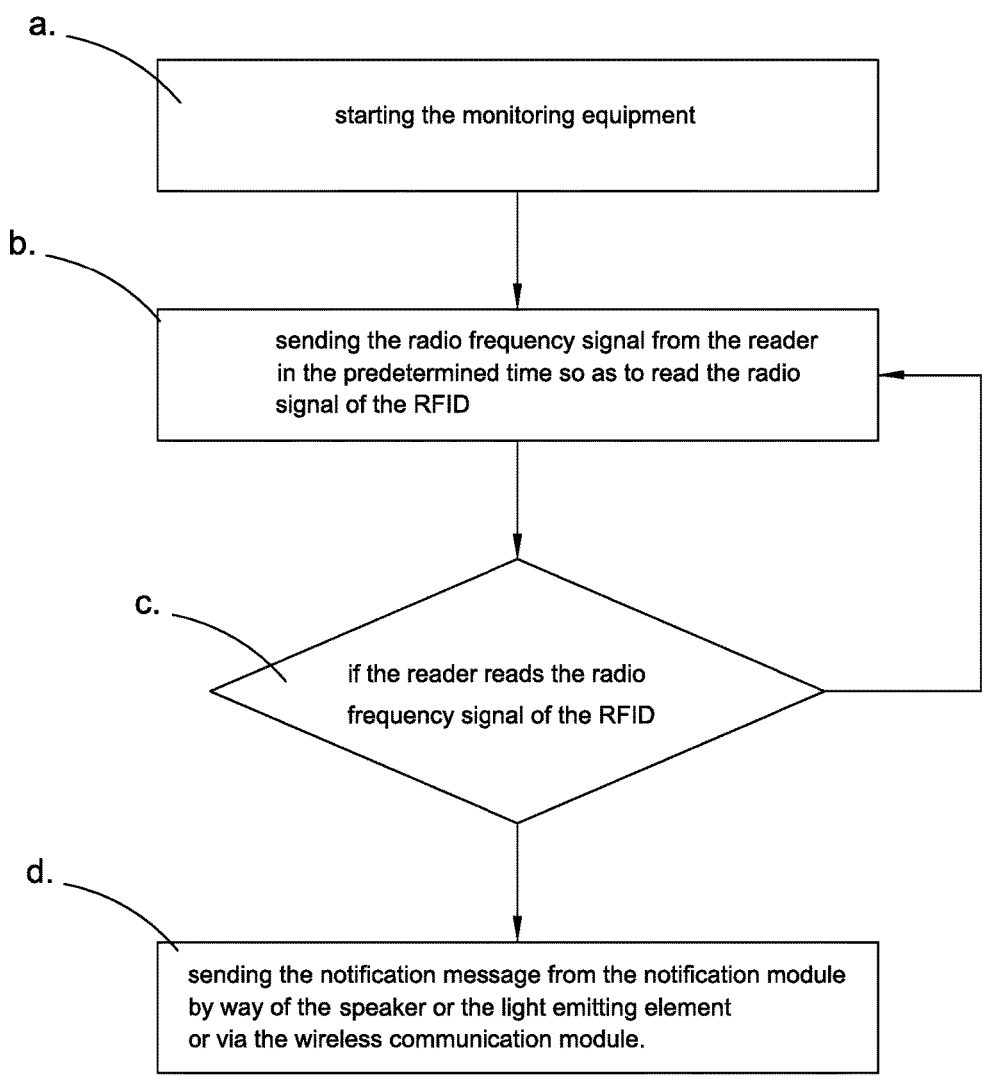
FIG. 8 is a flow chart showing the operation of the wireless detectable diaper and the monitoring equipment according to another preferred embodiment of the present invention.

With reference to FIG. 8, a method of operating the body 10 and the monitoring equipment 30 of the body 10 contains steps of:

(a). starting the monitoring equipment 30;

(b). sending the radio frequency signal from the reader 31 in the predetermined time so as to read the radio signal of the RFID tag 20;

(c). sending the electric signal to the notification module 33 after the reader 31 reads the radio frequency signal of the RFID tag 20, wherein when the reader 31 does not read the radio frequency signal of the RFID tag 20, an operating step of the method returns back to the step of (b); and (d). sending the notification message from the notification module 33 by way of the speaker 34 or the light emitting element 35 or via the wireless communication module 36.

In another embodiment, in the step (d), the notification module 33 starts the camera 40 to take the image and to send the image to the display device of the monitoring equipment 30 so that the user views the image.

Figure 9:
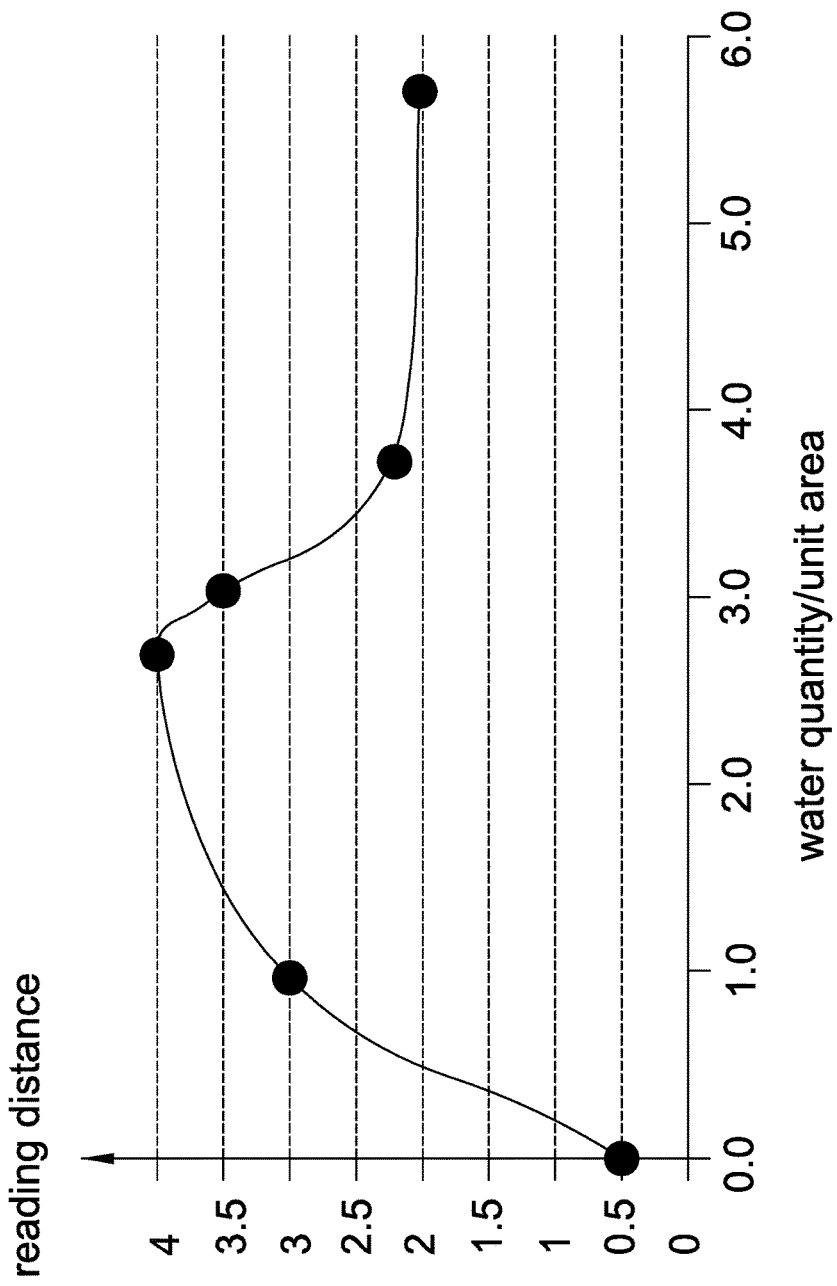
FIG. 9 is a schematic view showing experimental data of the wireless detectable diaper and the monitoring equipment according to the preferred embodiment of the present invention.

FIG. 9 shows experimental data of the body 10, i.e. read distances of the RFID tag 20 in different humidity of the body 10. When water of 1 mg exits in a unit area ($cm^2$) of the substrate 23 of the extending part 222 of the RFID tag 20, the read distance increases to 3 m from 0.5 m. When water of 2.6 mg exits in the unit area ($cm^2$) of the substrate 23, the read distance increases to 4 m. When the water in the unit area ($cm^2$) of the substrate 23 increases, the read distance reduces because water absorption from electromagnetic waves is higher than frequency deviation, thus obtaining balance read distance of 2 m.

The dielectric coefficient of the substrate 23 is changed, after the substrate 23 absorbs the urine or the water and the water absorbs the radio wave, hence the first frequency reading section of the antenna 22 of the RFID tag 20 has the frequency deviation. After the substrate 23 of the extending part 222 of the substrate 23 gets wet, the first frequency reading section of the antenna 22 of the RFID tag 20 offsets to the second frequency reading section R (represented by the solid line L3 of FIG. 3) of the monitoring equipment 30, hence the read distance (e.g. 3 m) of the RFID tag 20 increases.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A wireless detectable diaper sending a radio signal which being read by monitoring equipment, and the wireless detectable diaper comprising:

a body and a shiftable-frequency Radio-frequency identification (RFID) tag, and the body including a water-permeable lining layer, a waterproof layer, and an absorption layer defined between the lining layer and the waterproof layer and configured to absorb urine or water;

the RFID tag being a passive ultra-high frequency (UHF) RFID tag and including a chip and an antenna electrically connected with the chip, wherein the antenna has a main part and an extending part, the extending part is arranged on a water-absorbing substrate, the extending part and the substrate contact with the absorption layer of the body, the extending part and the substrate are arranged on a wetting position of the body, and the main part and the chip are arranged on a non-wetting position of the body;

wherein when the body is not wet, a first frequency reading section of the antenna departs from a second frequency reading section of the monitoring equipment;

wherein when the substrate absorbs the urine or the water in the absorption layer and is soaked by the urine or the water, a dielectric coefficient of the substrate is changed, and frequency deviates to the second frequency reading section of the monitoring equipment from the first frequency reading section of the antenna.

2. The wireless detectable diaper as claimed in claim 1, wherein the substrate is made of any one of paper, fabric, plastic, fiber, and wood pulp.

3. The wireless detectable diaper as claimed in claim 1, wherein the second frequency reading section of the monitoring equipment is within 820 MHz to 966 MHz.

4. The wireless detectable diaper as claimed in claim 1, wherein the antenna is printed on the substrate and is made of conductive ink.

5. The wireless detectable diaper as claimed in claim 1, wherein the extending part and the substrate are defined between the absorption layer and the waterproof layer or are defined between the absorption layer and the lining layer.

6. A wireless detectable diaper and monitoring equipment of the wireless detectable diaper comprising:
   a body and a shiftable-frequency Radio-frequency identification (RFID) tag, and the body including a water-permeable lining layer, a waterproof layer, and an absorption layer defined between the lining layer and the waterproof layer and configured to absorb urine or water;
   the RFID tag being a passive ultra-high frequency (UHF) RFID tag and including a chip and an antenna electrically connected with the chip, wherein the antenna has a main part and an extending part, the extending part is arranged on a water-absorbing substrate, the extending part and the substrate contact with the absorption layer of the body, the extending part and the substrate are arranged on a wetting position of the body, and the main part and the chip are arranged on a non-wetting position of the body;
   wherein when the body is not wet, a first frequency reading section of the antenna departs from a second frequency reading section of the monitoring equipment;
   wherein when the substrate absorbs the urine or the water in the absorption layer and is soaked by the urine or the water, a dielectric coefficient of the substrate is changed, and frequency deviates to the second frequency reading section of the monitoring equipment from the first frequency reading section of the antenna;
   the monitoring equipment including a reader, a reading antenna electrically connected with the reader, and a notification module electrically connected with the reader, wherein the reader reads a radio signal of the RFID tag via the reading antenna, and the reader sends an electrical signal to the notification module, thereafter the notification module sends a notification message so as to indicate that the body gets wet.

7. The wireless detectable diaper as claimed in claim 6, wherein the substrate is made of any one of paper, fabric, plastic, fiber, and wood pulp.

8. The wireless detectable diaper as claimed in claim 6, wherein the second frequency reading section of the monitoring equipment is within 820 MHz to 966 MHz.

9. The wireless detectable diaper as claimed in claim 6, wherein the antenna is printed on the substrate and is made of conductive ink.

10. The wireless detectable diaper as claimed in claim 6, wherein the extending part and the substrate are defined between the absorption layer and the waterproof layer or are defined between the absorption layer and the lining layer.

11. The wireless detectable diaper as claimed in claim 6, wherein the monitoring equipment also includes at least one of the speaker and the light emitting element, the speaker and the light emitting element are electrically coupled with the notification module so that the notification module sends the notification message to the speaker or/and the light emitting element and the speaker or/and the light emitting element make sounds or/and emit lights.

12. The wireless detectable diaper as claimed in claim 6, wherein the monitoring equipment includes a wireless communication module electrically connected with the notification module, wherein after the reader reads the radio signal of the RFID tag, it sends an electric signal to the notification module, and the notification module transmits the notification message to an electronic device via the wireless communication module.

13. The wireless detectable diaper as claimed in claim 12, wherein the wireless communication module is a bluetooth communication module or a Wi-Fi communication module.

14. The wireless detectable diaper as claimed in claim 6, wherein the monitoring equipment further includes a camera communicatively connected with the notification module, and the camera takes an image after the notification module transmits the notification message which is the body gets wet.

15. The wireless detectable diaper as claimed in claim 12, wherein the monitoring equipment further includes a camera communicatively connected with the notification module, and the camera takes an image after the notification module transmits the notification message which is the body gets wet.

16. The wireless detectable diaper as claimed in claim 14, wherein the camera is communicatively connected with the notification module in a wired signal transmission manner or a wireless signal transmission manner.

* * * * *